United States Patent [19]
Andrés-Gil et al.

[11] Patent Number: 6,156,747
[45] Date of Patent: Dec. 5, 2000

[54] ISOXAZOLIDINE DERIVATIVES

[75] Inventors: José Ignacio Andrés-Gil; Pedro Martinez-Jiménez, both of Madrid; Francisco Javier Fernández-Gadea, Toledo, all of Spain; Victor Karel Sipido, Merksem, Belgium

[73] Assignee: Janssen Pharmaceutica N.V., Belgium

[21] Appl. No.: 09/155,839

[22] PCT Filed: Apr. 9, 1997

[86] PCT No.: PCT/EP97/01830

§ 371 Date: Oct. 6, 1998

§ 102(e) Date: Oct. 6, 1998

[87] PCT Pub. No.: WO97/39001

PCT Pub. Date: Oct. 23, 1997

[30] Foreign Application Priority Data

Apr. 12, 1996 [EP] European Pat. Off. ............ 96200991

[51] Int. Cl.[7] ................ A61K 31/55; C07D 223/14; C07D 255/00; C07D 243/00; C07D 498/22

[52] U.S. Cl. .............. 514/214.01; 514/219; 540/543; 540/554; 540/555; 540/576; 540/578

[58] Field of Search ................ 514/214, 219, 514/214.01; 540/554, 555, 576, 578, 543

[56] References Cited

U.S. PATENT DOCUMENTS 4,039,558  8/1977  van der Burg et al. ............ 260/326.5

FOREIGN PATENT DOCUMENTS

| | | |
|---|---|---|
| 0 421 823 A2 | 4/1991 | European Pat. Off. . |
| WO 96/14320 | 5/1996 | WIPO . |
| WO 96/14321 | 5/1996 | WIPO . |

OTHER PUBLICATIONS

R.B. Moffett, "Tetracyclic Heterocycles as CNS Agents", J. Het. Chem 1980, vol. 17, No. 2, pp. 341–50.

G. Pandey et al., "Photosensitized Single Electron Transfer Oxidation of N–Hydroxylamines: A Convenient Synthesis of Cyclic Nitrones", 1987, vol. 28, No. 23, pp. 2649–2652 Tet. Letters.

S. A. Ali et al., "The 1,3–Dipolar Cycloaddition Reactions of 3,4,5,6–Tetrahydro–2H–Azepine 1–oxide", 1990, vol. 46, No. 20, Tetrahedron, pp. 7202–18.

J. J. Tufariello et al., "A Highly Steroselective Synthesis of (E,E)–1,5–Dienes", Tetrahedron Letters, 1987, vol. 28, No. 3, pp. 263–6.

J. J. Tufariello et al., "The Synthesis and Cycloaddition Reactions of 3–Azabicyclo [3.1.0] hex–2–ene 3–oxide and 3–Azabicyclo [3.2.0] hept–2–ene 3–oxide. Highly strained Bicyclic Nitrones", 1987, vol. 28, No. 3, pp. 267–70 Tetrahedron Letters.

S. Y. Rhie, "Synthesis of 3'–C–Isoxazoline,—Isoxazolidine, and —Alkoxyimine Derivatives derived from 3'–Deoxy–3'–C–Formylthymidine", Korean J. of Med. Chem., 1997, vol. 7, No. 1, pp. 29–33.

A. Hassan et al., "Nitrogen Inversion and N–O Bond Rotation in Some Hydroxylamine and Isoxalidine Derivatives", J. Chem. Soc., Perkin Trans.2, 1997, pp. 411–418.

Primary Examiner—Mukund J. Shah
Assistant Examiner—Brenda Coleman
Attorney, Agent, or Firm—Mary Appollina

[57] ABSTRACT

This invention concerns the compounds of formula (I),

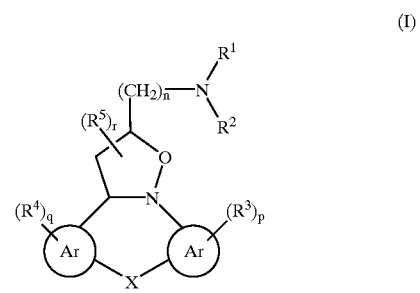

the N-oxide forms, the pharmaceutically acceptable addition salts and the stereochemically isomeric forms thereof, wherein n is zero to 6; p is zero to 3; q is zero to 3; r is zero to 3; $R^1$ and $R^2$ each independently are hydrogen; optionally substituted $C_{1-6}$alkyl; $C_{1-6}$alkylcarbonyl; trihalomethylcarbonyl; or $R^1$ and $R^2$ taken together with the nitrogen atom to which they are attached may form a morpholinyl ring or an optionally substituted heterocycle; each $R^3$ and $R^4$ independently are halo, cyano, hydroxy, trihalomethyl, trihalomethoxy, carboxyl, nitro, amino, mono- or di($C_{1-6}$alkyl)amino, $C_{1-6}$alkylcarbonylamino, aminosulfonyl, mono- or di($C_{1-6}$alkyl)-aminosulfonyl, $C_{1-6}$alkyl, $C_{1-6}$alkyloxy, $C_{1-6}$alkylcarbonyl or $C_{1-6}$alkyloxycarbonyl; each $R^5$ independently is $C_{1-6}$alkyl, cyano or trihalomethyl; X is $CR^6R^7$, $NR^8$, O, S, S(=O) or S(=O)$_2$; each

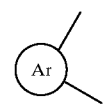

independently represents a bivalent aromatic heterocycle wherein the heterocycle may be selected from the group consisting of pyrrole, pyrrazole, imidazole, triazole, furane, thiophene, isoxazole, oxazole, isothiazole, thiazole, pyridine, pyridazine, pyrimidine, pyrazine and triazine; or one of the two bivalent aromatic heterocycles in the compounds of formula (I) may be 1,2-benzenediyl; and aryl is optionally substituted phenyl; it further relates to compositions comprising thesae compounds, as well as their use as therapeutic agents in the treatment or the prevention of CNS disorders, cardiovascular disorders or gastrointestinal disorders.

7 Claims, No Drawings

ISOXAZOLIDINE DERIVATIVES

CROSS REFERENCE TO RELATED APPLICATIONS

This application is a National Stage application under 35 U.S.C. § 371 of PCT/EP97/01830 filed Apr. 9, 1997

This invention concerns substituted tetracyclic isoxazolidine derivatives having antipsychotic, cardiovascular and gastrokinetic activity and their preparations; it further relates to compositions comprising them, as well as their use as a medicine.

U.S. Pat. No. 4,039,558 discloses pyrrolidinodibenzo-azepine, -oxazepine, -thiazepine and -diazepine derivatives having antihistamine, sedative and antidepressant properties. EP-A-0,421,823 describes dibenzopyrazino- or benzopyrido-pyrazino-azepine derivatives having anti-allergic and anti-asthmatic activities. The present compounds differ therefrom by the presence of an isoxazolidine ring, and by their pharmacological properties.

This invention concerns compounds of formula (I)

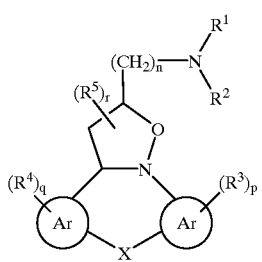
(I)

the N-oxide forms, the pharmaceutically acceptable addition salts and the stereochemically isomeric forms thereof, wherein:

n is zero, 1, 2, 3,4, 5, or 6;
p is zero, 1, 2 or 3;
q is zero, 1, 2 or 3;
r is zero, 1, 2 or 3;
$R^1$ and $R^2$ each independently are hydrogen; $C_{1-6}$alkyl; $C_{1-6}$alkylcarbonyl; trihalomethylcarbonyl; $C_{1-6}$alkyl substituted with hydroxy, $C_{1-6}$alkyloxy, carboxyl, $C_{1-6}$alkylcarbonyloxy, $C_{1-6}$alkyloxycarbonyl or aryl; or $R^1$ and $R^2$ taken together with the nitrogen atom to which they are attached may form a morpholinyl ring or a radical of formula:

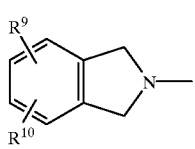
(a)

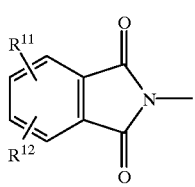
(b)

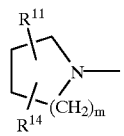
(c)

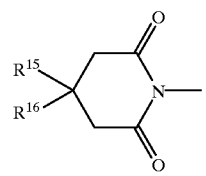
(d)

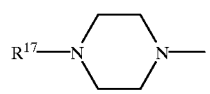
(e)

wherein:

$R^9$, $R^{10}$, $R^{11}$ and $R^{12}$ each independently are hydrogen, halo, trihalomethyl, or $C_{1-6}$alkyl;

m is zero, 1, 2, or 3;

$R^{13}$, $R^{14}$, $R^{15}$ and $R^{16}$ each independently are hydrogen or $C_{1-6}$alkyl; or $R^{15}$ and $R^{16}$ taken together may form a bivalent radical $C_{4-5}$alkanediyl;

$R^{17}$ is hydrogen; $C_{1-6}$alkyl; $C_{1-6}$alkylcarbonyl; trihalomethylcarbonyl; $C_{1-6}$alkyloxycarbonyl; aryl; di(aryl)methyl; $C_{1-6}$alkyl substituted with hydroxy, $C_{1-6}$alkyloxy, carboxyl, $C_{1-6}$alkylcarbonyloxy, $C_{1-6}$alkyloxycarbonyl or aryl;

each $R^3$ independently is halo, cyano, hydroxy, trihalomethyl, trihalomethoxy, carboxyl, nitro, amino, mono- or di($C_{1-6}$alkyl)amino, $C_{1-6}$alkylcarbonylamino, aminosulfonyl, mono- or di($C_{1-6}$alkyl)aminosulfonyl, $C_{1-6}$alkyl, $C_{1-6}$alkyloxy, $C_{1-6}$alkylcarbonyl or $C_{1-6}$alkyloxycarbonyl;

each $R^4$ independently is halo, cyano, hydroxy, trihalomethyl, trihalomethoxy, carboxyl, nitro, amino, mono- or di($C_{1-6}$alkyl)amino, $C_{1-6}$alkylcarbonylamino, aminosulfonyl, mono- or di($C_{1-6}$alkyl)aminosulfonyl, $C_{1-6}$alkyl, $C_{1-6}$alkyloxy, $C_{1-6}$alkylcarbonyl or $C_{1-6}$alkyloxycarbonyl;

each $R^5$ independently is $C_{1-6}$alkyl, cyano or trihalomethyl;

X is $CR^6R^7$, $NR^8$, Q, S, S(=O) or $S(=O)_2$; wherein $R^6$ and $R^7$ each independently are hydrogen, hydroxy, $C_{1-6}$alkyl, trihalomethyl, $C_{1-6}$alkyloxy or $R^6$ and $R^7$ taken together may form methylene; mono- or di(cyano)methylene; a bivalent radical of formula —$(CH_2)_2$—, —$(CH_2)_3$—, —$(CH_2)_4$—, —$(CH_2)_5$—, —O—$(CH_2)_2$—O—, —O—$(CH_2)_3$—O—; or, together with the carbon atom to which they are attached, a carbonyl;

$R^8$ is hydrogen, $C_{1-6}$alkyl, $C_{1-6}$alkylcarbonyl, arylcarbonyl, aryl$C_{1-6}$alkylcarbonyl, $C_{1-6}$alkylsulfonyl, arylsulfonyl or aryl$C_{1-6}$alkylsulfonyl;

each

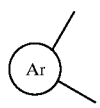

independently represents a bivalent aromatic heterocycle wherein the heterocycle may be selected from the group consisting of pyrrole, pyrrazole, imidazole, triazole, furane, thiophene, isoxazole, oxazole, isothiazole, thiazole, pyridine, pyridazine, pyrimidine, pyrazine and triazine; or one of the two bivalent aromatic heterocycles in the compounds of formula (1) may be 1,2-benzenediyl; and aryl is phenyl; or phenyl substituted with 1, 2 or 3 substituents selected from halo, hydroxy, $C_{1-6}$alkyl and trihalomethyl.

In the foregoing definitions $C_{1-6}$alkyl defines straight and branch chained saturated hydrocarbon radicals having from 1 to 6 carbon atoms such as, for example, methyl, ethyl, propyl, butyl, 1-methylpropyl, 1,1-dimethylethyl, pentyl, hexyl; $C_{4-5}$alkanediyl defines bivalent straight and branch chained saturated hydrocarbon radicals having from 4 to 5 carbon atoms such as, for example, 1,4-butanediyl, 1,5-pentanediyl; halo is generic to fluoro, chloro, bromo and iodo. The term monocyanomethylene stands for a radical of formula =CHCN, and dicyanomethylene for a radical of formula =C(CN)$_2$. The term halomethyl is meant to include mono-, di-, and trihalomethyl. Examples of halomethyl are fluoromethyl, difluoromethyl and 15 particularly trifluoromethyl. In case $R^6$ and $R^7$ taken together form a bivalent radical of formula —(CH$_2$)$_2$—, —(CH$_2$)$_3$—, —(CH$_2$)$_4$—, —(CH$_2$)$_5$—, —O—(CH$_2$)$_2$—O— or —O—(CH$_2$)$_3$—O—, the compounds of formula (I) are spiro compounds. The bivalent heterocyclic radicals in the definition of

include all bivalent radicals wherein the radical positions are adjacent on the heterocycle.

The pharmaceutically acceptable addition salts as mentioned hereinabove are meant to comprise the therapeutically active non-toxic base and acid addition salt forms which the compounds of formula (I) are able to form. The acid addition salt form of a compound of formula (I) that occurs in its free form as a base can be obtained by treating the base form of the compound of formula (I) with an appropriate acid such as an inorganic acid, for example, hydrohalic acid, e.g. hydrochloric or hydrobromic, sulfuric, nitric, phosphoric and the like acids; or an organic acid, such as, for example, acetic, hydroxyacetic, propanoic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formula (I) containing acidic protons may be converted into their therapeutically active non-toxic base, i.e. metal or amine, addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

Conversely said salt forms can be converted into the free forms by treatment with an appropriate base or acid.

The term addition salt as used hereinabove also comprises the solvates which the compounds of formula (I) as well as the salts thereof, are able to form. Such solvates are for example hydrates, alcoholates and the like.

The N-oxide forms of the compounds of formula (I) are meant to comprise those compounds of formula (I) wherein one or several nitrogen atoms are oxidized to the so-called N-oxide, particularly those N-oxides wherein the nitrogen bearing the $R^1$ and $R^2$ substituents is N-oxidized.

The term "stereochemically isomeric forms" as used hereinbefore and hereinafter defines all the possible isomeric forms in which the compounds of formula (I) may occur. Unless otherwise mentioned or indicated, the chemical designation of compounds denotes the mixture, and in particular the racemic mixture, of all possible stereochemically isomeric forms, said mixtures containing all diastereomers and enantiomers of the basic molecular structure. Stereochemically isomeric forms of the compounds of formula (I) and mixtures of such forms are obviously intended to be encompassed by formula (1).

The numbering of the isoxazolidine ring-system present in the compounds of formula (I), is used hereinafter as defined by Chemical Abstracts nomenclature. The compounds of formula (I) occur as cis and trans isomers. Said terms refer to the position of the substituents on the isoxazolidine ring and are also in accordance with Chemical Abstracts nomenclature. The nomenclature is unusual in that the only relevant substituent of carbon atom 3a is either hydrogen or $R^5$. When establishing the configuration, the substituent on carbon atom 3a and the substituent with the highest priority on carbon atom 2 (i.e. either —(CH$_2$)$_n$—NR$^1$R$^2$ or R$^5$) are considered. When the relevant substituent on carbon atom 3a and the substituent with the highest priority on carbon atom 2 are on the same side of the mean plane determined by the isoxazolidine ring then the configuration is designated cis, if not, the configuration is designated trans.

The compounds of formula (I) have at least two asymmetric centers, namely carbon atom 3a and carbon atom 2. Said asymmetric centers and any other asymmetric center which may be present, are indicated by the descriptors R and S. When a monocyanomethylene moiety is present in the compounds of formula (1), said moiety may have the E- or Z-configuration.

Whenever used hereinafter, the term "compounds of formula (I)" is meant to also include the pharmaceutically acceptable acid addition salts, base addition salts and all stereoisomeric forms, and also the N-oxide forms.

Interesting compounds are those compounds of formula (I) wherein one of the two

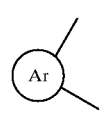

radicals is 1,2-benzenediyl; in particular those compounds of formula (I) wherein one of the two

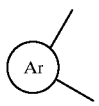

radicals is 1,2-benzenediyl and the other bivalent radical

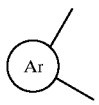

is a bivalent pyridine, imidazole, pyrrole or thiophene radical.

Other interesting compounds are those compounds of formula (I) wherein X is $CR^6R^7$ or O.

Still other interesting compounds are those compounds of formula (I) wherein r is zero.

Preferred compounds are those compounds of formula (I) wherein $R^1$ and $R^2$ are both methyl and n is 1 or 2.

Other preferred compounds are those compounds of formula (I) wherein $R^1$ and $R^2$ are taken together with the nitrogen atom to which they are attached to form a morpholinyl ring or a radical of formula (e).

Also preferred are those compounds of formula (I) wherein $R^1$ is hydrogen or $C_{1-6}$alkyl substituted with $C_{1-6}$alkylcarbonyloxy, $R^2$ is methyl and n is 1 or 2.

Most preferred compounds are:
2,3,3a,8-tetrahydro-N,N-dimethylisoxazolo[2,3-a]pyrrolo[2,1-c][1,4]benzodiazepine-2-methanamine;
2,3,3a,8-tetrahydro-N,N-dimethylimidazo[2,1-c]isoxazolo[2,3-a][1,4]benzodiazepine-2-methanamine;
2,3,3a,7-tetrahydro-N,N-dimethylisoxazolo[2,3-a]thieno[2,3-c][1]benzazepine-2-methanamine;
2,3,3a,7-tetrahydro-N,N-dimethylisoxazolo[2,3-a]thieno[3,2-c][1]benz-azepine-2-methanamine; the stereochemically isomeric forms and pharmaceutically acceptable addition salts thereof, and also the N-oxide forms thereof.

In general, the compounds of formula (I) may be prepared by a 1,3-dipolar cycloaddition of a dienophile of formula (III) and an intermediate of formula (II). In the intermediates (II) and (III) and in any other intermediate mentioned hereinunder, $R^1$ to $R^5$, X, n, r, p, q and

are as defined hereinabove, unless otherwise indicated.

Further, the hydrogens on the $sp^2$-hybridized aliphatic carbon atoms in the intermediates (II) and (III) may each individually be replaced by $R^5$. Said 1,3-dipolar cycloaddition may conveniently be carried out by mixing the reactants, optionally in a reaction-inert solvent such as, for example, toluene, 4-methyl-2-pentanone or tetrahydrofuran, or a mixture of such solvents. Stirring and elevated temperatures, or increased pressure may enhance the rate of the reaction. The reaction of intermediate (II) with intermediate (III) in practice is regioselective yielding compounds of formula (I).

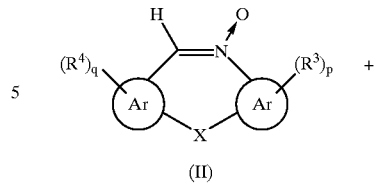

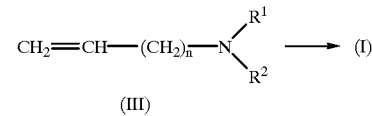

In this and the following preparations, the reaction products may be isolated from the reaction medium and, if necessary, further purified according to methodologies generally known in the art such as, for example, extraction, crystallization, trituration and chromatography.

The compounds of formula (I) may also be converted into each other following art-known transformation reactions. For instance,
a) a compound of formula (I), wherein $R^1$ and $R^2$ taken together with the nitrogen atom to which they are attached form a radical of formula (b), may be converted into the corresponding primary amine by treatment with hydrazine or aqueous alkali;
b) a compound of formula (I), wherein $R^1$ or $R^2$ is trifluoromethylcarbonyl, may be converted into the corresponding primary or secondary amine by hydrolysis with aqueous alkali;
c) a compound of formula (I), wherein $R^1$ or $R^2$ is $C_{1-6}$alkyl substituted with $C_{1-6}$alkylcarbonyloxy may be hydrolyzed into a compound of formula (I) wherein $R^1$ or $R^2$ is $C_{1-6}$alkyl substituted with hydroxy;
d) a compound of formula (I), wherein $R^1$ and $R^2$ are both hydrogen may be mono- or di-N-alkylated to the corresponding amine form;
e) a compound of formula (I), wherein $R^1$ and $R^2$ are both hydrogen may be N-acylated to the corresponding amide;
f) a compound of formula (I), containing a $C_{1-6}$alkyloxycarbonyl group may be hydrolyzed to the corresponding carboxylic acid.

In addition, the compounds of formula (I) wherein X is other than S may also be converted to the corresponding N-oxide forms following art-known procedures for converting a trivalent nitrogen into its N-oxide form. Said N-oxidation reaction may generally be carried out by reacting the starting material of formula (I) with 3-phenyl-2-(phenylsulfonyl)oxaziridine or with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example. benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The intermediates of formula (II) wherein $X^a$ is $CR^6R^7$, O, S(=O) or S(=O)$_2$, said intermediates are represented by formula (II-a), may be prepared by the oxidation of an intermediate of formula (IV) with a suitable oxidizing agent such as, for example, 2-benzenesulfonyl-3-phenyl-oxaziridine, hydrogen peroxide, tert-butyl hydroxyperoxide, or metachloroperbenzoic acid.

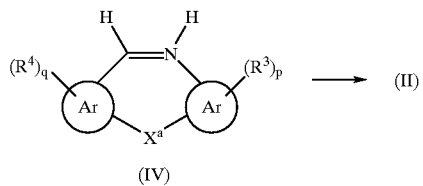

(IV)

Said oxidation is performed in a reaction-inert solvent at temperatures ranging between −20° C. and 50° C., preferably between 0° C. and room temperature. Suitable solvents are, for example, water, dichloromethane, toluene, methanol, 4-methyl-2-pentanone, or a mixture of such solvents. When using peroxide oxidants, the reaction rate may be enhanced by using metallic catalysts such as, for example, $Na_2WO_4$, $VO(acetylacetonate)2$, $Ti(OBu)_4$, or $MoO_2(acetylacetonate)2$, optionally under a reaction-inert atmosphere such as, for example, argon.

Alternatively, intermediates of formula (II) wherein $R^{3b}$ is the same as $R^3$ but other than nitro, and $R^{4b}$ is the same as $R^4$ but other than nitro, said intermediates are represented by formula (II-b), may be prepared by reducing the nitro group of an intermediate of formula (V) in the presence of water and a suitable reducing agent such as, for example, zinc or iron; subsequently followed by an in situ intramolecular cyclization in the presence of a weak acid such as, for example, ammoniumchloride or acetic acid. Said reductive cyclization is performed in a reaction-inert solvent such as, for example, 1,4-dioxane. Stirring and elevated temperatures may enhance the rate of the reaction. In intermediate (V), $R^{3b}$ and $R^{4b}$ are defined as in intermediates of formula (II-b) and both the formyl and nitro substituent are on an atom adjacent to the -X radical on the respective aromatic heterocycles of formula

as defined in the compounds of formula (I).

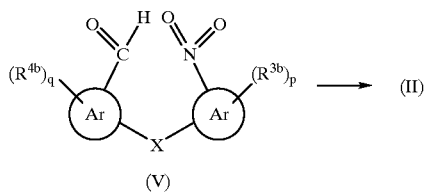

(V)

The intermediates of formula (II) wherein

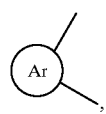

X, $R^3$, $R^4$, p and q are as defined hereinabove are deemed novel.

Pure stereochemically isomeric forms of the compounds of formula (I) may be obtained by the application of art-known procedures. Diastereomers may be separated by physical methods such as selective crystallization and chromatographic techniques, e.g. counter-current distribution, liquid chromatography and the like.

The compounds of formula (I) as prepared in the hereinabove described processes are generally racemic mixtures of enantiomers which can be separated from one another following art-known resolution procedures. The racemic compounds of formula (I) which are sufficiently basic or acidic may be converted into the corresponding diastereomeric salt forms by reaction with a suitable chiral acid respectively with a suitable chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of the present invention show affinity for $5-HT_2$ receptors, particularly for $5-HT_{2A}$ and $5-HT_{2C}$ receptors (nomenclature as described by D. Hoyer in "Serotonin (5-HT) in neurologic and psychiatric disorders" edited by M. D. Ferrari and published in 1994 by the Boerhaave Commission of the University of Leiden). The serotonin antagonistic properties of the present compounds may be demonstrated by their inhibitory effect in the "5-hydroxytryptophan Test on Rats" which is described in Drug Dev. Res., 13, 237–244 (1988). Furthermore, the present compounds show interesting pharmacological activity in vivo in the "mCPP Test on Rats" which is described hereinafter, in the "Elevated and Illuminated Plus Maze Test" which is described in Drug Dev. Res., 18, 119–144 (1989), and in the "Combined Apomorphine, Tryptamine, Norepinephrine (ATN) Test on Rats" which is described in Arch. Int. Pharmacodyn, 227, 238–253 (1977).

In view of these pharmacological and physicochemical properties, the compounds of formula (I) are useful as therapeutic agents in the treatment or the prevention of central nervous system disorders like anxiety, depression and mild depression, bipolar disorders, sleep- and sexual disorders, psychosis, borderline psychosis, schizophrenia, migraine, personality disorders or obsessive-compulsive disorders, social phobias or panic attacks, organic mental disorders, mental disorders in children, aggression, memory disorders and attitude disorders in older people, addiction, obesity, bulimia and similar disorders. In particular, the present compounds may be used as anxiolytics, antipsychotics, antidepressants, anti-migraine agents and as agents having the potential to overrule the addictive properties of drugs of abuse.

The compounds of formula (I) may also be used as therapeutic agents in the treatment of motoric disorders. It may be advantageous to use the present compounds in combination with classical therapeutic agents for such disorders.

The compounds of formula (I) may also serve in the treatment or the prevention of damage to the nervous system caused by trauma, stroke, neurodegenerative illnesses and the like; cardiovascular disorders like high blood pressure, thrombosis, stroke, and the like; and gastrointestinal disorders like dysfunction of the motility of the gastrointestinal system and the like.

In view of the above uses of the compounds of formula (1), it follows that the present invention also provides a method of treating warm-blooded animals suffering from such diseases, said method comprising the systemic administration of a therapeutic amount of a compound of formula (I) effective in treating the above described disorders, in particular, in treating anxiety, psychosis, depression, migraine and addictive properties of drugs of abuse.

The present invention thus also relates to compounds of formula (I) as defined hereinabove for use as a medicine, in particular, the compounds of formula (I) may be used for the manufacture of a medicine for treating anxiety, psychosis, depression, migraine and addictive properties of drugs of abuse.

Those of skill in the treatment of such diseases could determine the effective therapeutic daily amount from the test results presented hereinafter. An effective therapeutic daily amount would be from about 0.01 mg/kg to about 10 mg/kg body weight, more preferably from about 0.05 mg/kg to about 1 mg/kg body weight.

For ease of administration, the subject compounds may be formulated into various pharmaceutical forms for administration purposes. To prepare the pharmaceutical compositions of this invention, a therapeutically effective amount of the particular compound, optionally in addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils. alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing compounds of formula (I) may be formulated in an oil for prolonged action. Appropriate oils for this purpose are, for example, peanut oil, sesame oil, cottonseed oil, corn oil, soy bean oil, synthetic glycerol esters of long chain fatty acids and mixtures of these and other oils. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. Acid or base addition salts of compounds of formula (I) due to their increased water solubility over the corresponding base or acid form, are obviously more suitable in the preparation of aqueous compositions.

In order to enhance the solubility and/or the stability of the compounds of formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin. Also co-solvents such as alcohols may improve the solubility and/or the stability of the compounds of formula (I) in pharmaceutical compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect, in association with the required pharmaceutical carrier. Examples of such dosage unit forms are tablets (including scored or coated tablets). capsules, pills, powder packets, wafers, injectable solutions or suspensions, teaspoonfuls, tablespoonfuls and the like, and segregated multiples thereof.

The following examples are intended to illustrate and not to limit the scope of the present invention.

Experimental part
A. Preparation of the intermediate compounds

EXAMPLE A.1 a) Sodium hydride (60%) (0.0899 mol) was added portionwise under $N_2$ at room temperature to a mixture of 2-hydroxybenzaldehyde (0.0818 mol) in N,N-dimethylformamide and the mixture was stirred under $N_2$ for 15 minutes. 2-Chloro-3-nitro-pyridine (0.0818 mol) in N,N-dimethylformamide was added and the mixture was stirred at 100° C. for 2 hours. The mixture was poured into ice/water, extracted with diethylether and the solvent was evaporated, yielding 4.5 g (23%) of 2-[(3-nitro-2-pyridinyl)oxy]benzaldehyde (interm. 1).

b) Zinc (0.0821 mol) was added to a suspension of intermediate (1) (0.0158 mol) in 1,4-dioxane (100 ml) and water (6.2 ml). Ammonium chloride (0.0413 mol) was added dropwise at 5–7° C. and the mixture was stirred at 5° C. for 1 hour. The precipitate was filtered off and the filtrate was evaporated. The residue (6.6 g) was treated with water, extracted with $CH_2Cl_2$ and the solvent was evaporated. The product was used without further purification, yielding 3.7 g of pyrido[2,3-b][1,4]benzoxazepine, 5-oxide (interm. 2).

EXAMPLE A.2 a) A mixture of 2-aminobenzyl alcohol (0.1218 mol), 3-thiophenecarboxaldehyde (0.1218 mol) and molecular sieves (3 Å) in 2-propanol (150 ml) was stirred overnight at room temperature. The crude reaction mixture was filtered, the residue was treated with $CH_2Cl_2$, and the mixture was filtered again. The solvent was evaporated, yielding 21.53 g (81%) of (±)-1,4-dihydro-2-(3-thienyl)-2H-3,1-benzoxazine (interm. 3).

b) Sodium tetrahydroborate (0.1979 mol) was added portionwise to intermediate (3) (0.0989 mol) in ethanol (230 ml), stirred at room temperature. The reaction mixture was stirred for 30 minutes at room temperature, then for 90 minutes at reflux temperature. The solvent was evaporated, the residue was treated with a saturated aqueous $NH_4Cl$ solution, and the resulting mixture was extracted with $CH_2Cl_2$. The separated organic layer was dried, filtered and the solvent evaporated, yielding 20.89 g (85%) of 2-[(3-thienylmethyl)amino]benzenemethanol (interm. 4).

c) Tin (IV) chloride (0.2658 mol) was added dropwise to intermediate (4) (0.088 mol) in 1,2-dichloroethane (1000 ml). The reaction mixture was stirred for one hour at 80° C. The reaction mixture was cooled on an ice bath. Water was added dropwise and the resulting solution was basified, then extracted with $CH_2Cl_2$. The separated organic layer was dried, filtered and the solvent evaporated. The residue was purified by flash column chromatography over silica gel (eluent: hexane/ethylacetate 9/1 and 8/2). The desired fractions were collected and the solvent was evaporated, yielding 4.76 g (27%) of 5,10-dihydro-4H-thieno[3,2-c][1]benzazepine (interm. 5).

d) Intermediate (5) (0.0145 mol) was dissolved in $CH_2Cl_2$ (128 ml) and cooled on an ice bath. (±)-3-Phenyl-2-(phenylsulfonyl)oxaziridine (0.02911 mol) was added portionwise and the reaction mixture was stirred for 4 hours. The solvent was evaporated and the residue was purified by open column chromatography over silica gel (eluent: $CH_2Cl_2/CH_3OH$ 100/0 and 96/4). The pure fractions were collected and vent was evaporated, yielding 3.64 g (82%) 10H-thieno[3,2-c][1]benzazepine, 5-oxide (interm. 6).

Tables 1 and 2 list the intermediates of formula (II) which were made according to one of the above examples (column Ex. No.).

TABLE 1

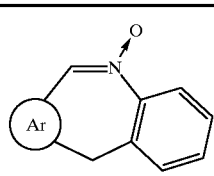

| Interm. No. | Ex. No. | Ar |
|---|---|---|
| 6 | A.2 | (2-methyl-3-thienyl) |
| 7 | A.1 | (2-methyl-1-pyrrolyl) |
| 8 | A.1 | (1-methyl-2-imidazolyl) |
| 9 | A.2 | (3-methyl-2-thienyl) |
| 10 | A.2 | (2-methyl-3-pyridinyl) |

TABLE 2

| Interm. No. | Ex. No. | X | Ar |
|---|---|---|---|
| 2 | A.1 | O | (2-methyl-3-pyridinyl) |
| 11 | A.2 | $CH_2$ | (3-methyl-4-pyridinyl) |

B. Preparation of the compounds of formula (I)

EXAMPLE B.1

A mixture of intermediate (2) (0.0174 mol) and 3-amino-1-propene (0.0261 mol) in tetrahydrofuran (60 ml) was stirred at 60° C. for 5 hour. The solvent was evaporated and the residue was purified by flash chromatography over silica gel (eluent: $CH_2Cl_2$/hexane/2-propapnone 6/3/1 and CH₂Cl₂/hexane/CH₃OH 6/3.5/0.5). The pure fractions were collected and the solvent evaporated. The residue (2.5 g) was washed with diethylether and purified further by HPLC (eluent: hexane/CH₂Cl₂/CH₃OH 6/3/1). The pure fractions were collected and evaporated, yielding 1.4 g (27%) of (±)-cis-3,13b-dihydro-N,N-dimethyl-2H-isoxazolo[2,3-d]pyrido[2,3-b][1,4]benzoxazepine-2-methanamine (comp. 1; mp. 106.3° C.).

EXAMPLE B.2

(±)-cis-2,3,3a,7-tetrahydro-N,N-dimethyl isoxazolo[2,3-a]thieno[3,2-c][1]benzazepine-2-methanamine ethanedioate (1:1) (comp. 2; mp. 136.9° C.) was prepared in a similar way as compound 1 in example B.1 but using toluene as a solvent.

EXAMPLE B.3

(±)-cis-2,3,3a,8-tetrahydro-N,N-dimethylisoxazolo[2,3-a]pyrrolo[2,1-c][1,4]-benzodiazepine-2-methanamine ethanedioate (1:1) (comp. 3; mp. 137.6° C.) was prepared in a similar way as compound 1 in example B.1 but using a mixture of tetrahydrofuran and toluene as a solvent.

EXAMPLE B.4

2-(methyl-2-propenylamino)ethanol acetate(ester) (0.0176 mol) was added to a solution of intermediate (11) (0.0160 mol) in tetrahydrofuran (110 ml) and the resulting reaction mixture was stirred and refluxed for 24 hours. Toluene (100 ml) was added and the mixture was stirred and refluxed for 24 hours. The solvent was evaporated and the residue was purified by short open column chromatography over silica gel (eluent: CH₂Cl₂/(CH₃OH/NH₃) 96/4), then by HPLC (eluent: CH₂Cl₂/CH₃OH 96/4). The pure fractions were collected and the solvent was evaporated, yielding 0.360 g (10%) of (±)-2,3,3a,8-tetrahydro-2-(4-morpholinylmethyl)isoxazolo[3,2-a]pyrido[3,4-c][2]-benzazepine (comp. 9; mp. 46° C.).

Tables 3 and 4 list the compounds of formula (I) which were made according to one of above examples (column "Ex. No.").

TABLE 3

| Co. No | Ex. No. | Ar | physical data |
|---|---|---|---|
| 2 | B.2 | thiophene (2,3-linked) | (±)-cis; mp. 136.9° C.; oxalic acid (1:1) |
| 3 | B.3 | pyrrole (N-methyl) | (±)-cis; mp. 137.6° C.; oxalic acid (1:1) |
| 4 | B.1 | imidazole (N-methyl) | (±)-cis; mp. 135.5° C.; H₂O (1:2). HCl (1:2) |
| 5 | B.2 | thiophene | (±)-cis; mp. 157.8° C.; oxalic acid (1:1) |
| 6 | B.1 | pyridine (methyl) | mp. 112.5° C.; oxalic acid (1:1).H₂O (1:1).2-propanolate (1:1) |

TABLE 4

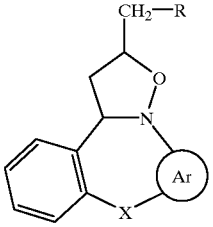

| Co. No. | Ex. No. | X | R | Ar | Physical data |
|---|---|---|---|---|---|
| 1 | B.1 | O | —N(CH$_3$)$_2$ |  | (±)-cis; mp. 106.3° C. |
| 7 | B.1 | CH$_2$ | —N(CH$_3$)$_2$ | 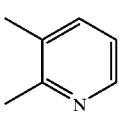 | (±)-cis |
| 8 | B.1 | CH$_2$ | 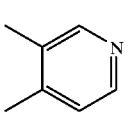 CH$_3$—C(O)—O—CH$_2$—CH$_2$—N(CH$_3$)— | 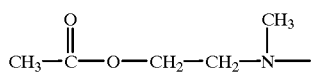 | (±)-cis |
| 9 | B.4 | CH$_2$ | 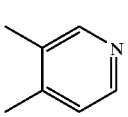 | 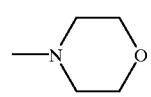 | (±)-cis; mp. 46° C. |
| 10 | B.1 | CH$_2$ | 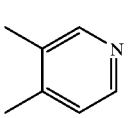 | 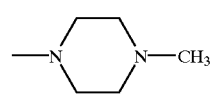 | (±)-cis; mp. 116° C. |

C. Pharmacological example

EXAMPLE C.1

"mCPP Test on Rats"

Rats were treated with the test compound at a dose varying between 0.0025 mg/kg and 40 mg/kg body weight at pre-test time T of 1 hour, and with 1 mg/kg mCPP (metachlorophenylpiperazine), injected intravenously, 15 minutes prior to the test. After pre-test time T elapsed, treated rats were submitted to the "Open Field Test on Rats" as described in Drug Dev. Res. 18, 119–144 (1989), but using an infra-red light source instead of a Kleverlux® (12V/20 W) light source. A dose at which 42% of the tested rats showed suppression of the mCPP induced effects, i.e. mCPP-antagonism, was defined as an active dose. Compound numbers 2, 3 and 7 were active at a test dose of 10 mg/kg or less.

EXAMPLE C.2

"Elevated and Illuminated Plus Maze Test on Rats"

The "Elevated and Illuminated Plus Maze Test on Rats" is described in Drug Dev. Res. 18, 119–144 (1989). An active dose of a test compound in said test was defined as a dose at which 42% of the tested rats explored the illuminated arms of the maze. The compounds numbers 2, 4 and 5 showed activity at a test dose of 2.5 mg/kg or less.

EXAMPLE C.3

In vitro Binding Affinity for 5-HT$_{2A}$ and 5-HT$_{2C}$ receptors

The interaction of the compounds of formula (I) with 5-HT$_{2A}$ and 5-HT$_{2C}$ receptors was assessed in in vitro radioligand binding experiments.

In general, a low concentration of a radioligand with a high binding affinity for the receptor is incubated with a sample of a tissue preparation enriched in a particular receptor (1 to 5 mg tissue) in a buffered medium (0.2 to 5 ml). During the incubation, the radioligands bind to the receptor. When equilibrium of binding is reached, the receptor bound radioactivity is separated from the non-bound radioactivity, and the receptor bound activity is counted. The interaction of the test compounds with the receptors is assessed in competition binding experiments. Various concentrations of the test compound are added to the incubation mixture containing the tissue preparation and the radioligand. Binding of the radioligand will be inhibited by the test compound in proportion to its binding affinity and its concentration.

The radioligand used for 5-HT$_{2A}$ binding affinity is $^3$H-ketanserin and the tissue used is the frontal cortex of the rat. At a test concentration of 10$^{-7}$ M, the compounds with number 2, 3, 5, and 7 produced an inhibition of the 5-HT$_{2A}$ receptor of more than 40%, and the other compounds produced an inhibition of less than 40%.

The radioligand used for 5-HT$_{2C}$ binding affinity is $^3$H-mesulergine and the tissue used is the choroid plexus of the pig. At a test concentration of 10$^{-7}$ M, the compounds with number 2, 3, 5, 6, and 7 produced an inhibition of the 5-HT$_{2C}$ receptor of more than 40%, and the other compounds produced an inhibition of less than 40%.

D. Composition examples

"Active ingredient" (A.I.) as used throughout these examples relates to a compound of formula (I), a pharmaceutically acceptable acid addition salt, a stereochemically isomeric form thereof or a N-oxide form thereof.

EXAMPLE D.1

Oral Solution

Methyl 4-hydroxybenzoate (9 g) and propyl 4-hydroxybenzoate (1 g) were dissolved in boiling purified water (4 l). In 3 l of this solution were dissolved first 2,3-dihydroxybutanedioic acid (10 g) and thereafter A.I (20 g). The latter solution was combined with the remaining part of the former solution and 1,2,3-propanetriol (121) and sorbitol 70% solution (3 l) were added thereto. Sodium saccharin (40 g) were dissolved in water (500 ml) and raspberry (2 ml) and gooseberry essence (2 ml) were added. The latter solution was combined with the former, water was added q.s. to a volume of 20l providing an oral solution comprising 5 mg of the active ingredient per teaspoonful (5 ml). The resulting solution was filled in suitable containers.

EXAMPLE D.2

Film-coated Tablets

Preparation of tablet core

A mixture of A.I. (100 g), lactose (570 g) and starch (200 g) was mixed well and thereafter humidified with a solution of sodium dodecyl sulfate (5 g) and polyvinylpyrrolidone (10 g) in water (200 ml). The wet powder mixture was sieved, dried and sieved again. Then there was added microcrystalline cellulose (100 g) and hydrogenated vegetable oil (15 g). The whole was mixed well and compressed into tablets, giving 10,000 tablets, each containing 10 mg of the active ingredient.

Coating

To a solution of methyl cellulose (10 g) in denaturated ethanol (75 ml) there was added a solution of ethyl cellulose (5 g) in dichloromethane (150 ml). Then there were added dichloromethane (75 ml) and 1,2,3-propanetriol (2.5 ml). Polyethylene glycol (10 g) was molten and dissolved in dichloromethane (75 ml). The latter solution was added to the former and then there were added magnesium octadecanoate (2.5 g), polyvinylpyrrolidone (5 g) and concentrated colour suspension (30 ml) and the whole was homogenated. The tablet cores were coated with the thus obtained mixture in a coating apparatus.

EXAMPLE D.3

Injectable Solution

Methyl 4-hydroxybenzoate (1.8 g) and propyl 4-hydroxybenzoate (0.2 g) were dissolved in boiling water (500 ml) for injection. After cooling to about 50° C. there were added while stirring lactic acid (4 g). propylene glycol (0.05 g) and A.I. (4 g). The solution was cooled to room temperature and supplemented with water for injection q.s. ad 1 l, giving a solution comprising 4 mg/ml of A.I. The solution was sterilized by filtration and filled in sterile containers.

What is claimed is:

1. A compound of formula

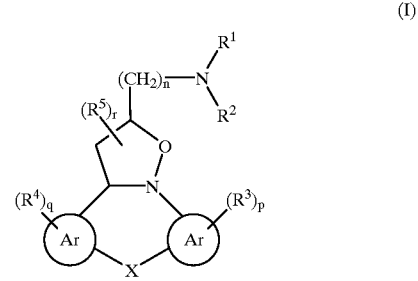

(I)

a N-oxide form, a pharmaceutically acceptable addition salt or a stereochemically isomeric form thereof, wherein n is zero, 1, 2, 3, 4, 5, or 6;

p is zero, 1, 2 or 3;

q is zero, 1, 2 or 3;

r is zero, 1, 2 or 3;

R$^1$ and R$^2$ each independently are hydrogen; C$_{1-6}$alkyl; C$_{1-6}$alkylcarbonyl; trihalomethylcarbonyl; C$_{1-6}$alkyl substituted with hydroxy, C$_{1-6}$alkyloxy, carboxyl, C$_{1-6}$alkylcarbonyloxy, C$_{1-6}$alkyloxycarbonyl or aryl; or R$^1$ and R$^2$ taken together with the nitrogen atom to which they are attached may form a morpholinyl ring or a radical of formula:

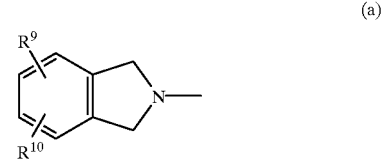

(a)

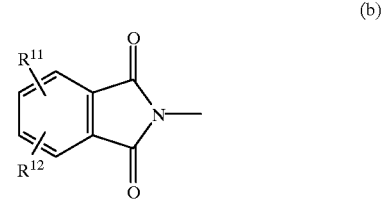

(b)

(c)

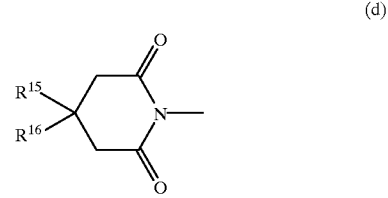

(d)

(e)

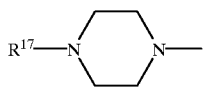

wherein
$R^9$, $R^{10}$, $R^{11}$ and $R^{12}$ each independently are hydrogen, halo, trihalomethyl, or $C_{1-6}$alkyl;
m is zero, 1, 2, or 3;
$R^{13}$, $R^{14}$, $R^{15}$ and $R^{16}$ each independently are hydrogen or $C_{1-6}$alkyl; or
$R^{15}$ and $R^{16}$ taken together may form a bivalent radical $C_{4-5}$alkanediyl;
$R^{17}$ is hydrogen; $C_{1-6}$alkyl; $C_{1-6}$alkylcarbonyl; trihalomethylcarbonyl;
$C_{1-6}$alkyloxycarbonyl; aryl; di(aryl)methyl; $C_{1-6}$alkyl substituted with hydroxy,
$C_{1-6}$alkyloxy, carboxyl, $C_{1-6}$alkylcarbonyloxy, $C_{1-6}$alkyloxycarbonyl or aryl;
each $R^3$ independently is halo, cyano, hydroxy, trihalomethyl, trihalomethoxy, carboxyl, nitro, amino, mono- or di($C_{1-6}$alkyl)amino, $C_{1-6}$alkylcarbonylamino, aminosulfonyl, mono- or di($C_{1-6}$alkyl)aminosulfonyl, $C_{1-6}$alkyl, $C_{1-6}$alkyloxy, $C_{1-6}$alkylcarbonyl or $C_{1-6}$alkyloxycarbonyl;
each $R^4$ independently is halo, cyano, hydroxy, trihalomethyl, trihalomethoxy, carboxyl, nitro, amino, mono- or di($C_{1-6}$alkyl)amino, $C_{1-6}$alkylcarbonylamino, aminosulfonyl, mono- or di($C_{1-6}$alkyl)aminosulfonyl, $C_{1-6}$alkyl, $C_{1-6}$alkyloxy, $C_{1-6}$alkylcarbonyl or $C_{1-6}$alkyloxycarbonyl;
each $R^5$ independently is $C_{1-6}$alkyl, cyano or trihalomethyl;
X is $CR^6R^7$; wherein
$R^6$ and $R^7$ each independently are hydrogen, hydroxy, $C_{1-6}$alkyl, trihalomethyl, $C_{1-6}$alkyloxy or $R^6$ and $R^7$ taken together may form methylene; mono- or di(cyano)methylene; a bivalent radical of formula —(CH$_2$)$_2$—, —(CH$_2$)$_3$—, —(CH$_2$)$_4$—, —(CH$_2$)$_5$—, —O—(CH$_2$)$_2$—O—, —O—(CH$_2$)$_3$—O—; or, together with the carbon atom to which they are attached, a carbonyl;
$R^8$ is hydrogen, $C_{1-6}$alkyl, $C_{1-6}$alkylcarbonyl, arylcarbonyl, aryl$C_{1-6}$alkylcarbonyl, $C_{1-6}$alkylsulfonyl, arylsulfonyl or aryl$C_{1-6}$alkylsulfonyl;
each

independently represents a bivalent aromatic heterocycle wherein the heterocycle may be selected from the group consisting of pyrrole, pyrrazole, imidazole, triazole, furane, thiophene, isoxazole, oxazole, isothiazole, thiazole, pyridine, pyridazine, pyrimidine, pyrazine and triazine; or one of the two bivalent aromatic heterocycles in the compounds of formula (I) may be 1,2-benzenediyl; and aryl is phenyl; or phenyl substituted with 1, 2 or 3 substituents selected from halo, hydroxy, $C_{1-6}$alkyl and trihalomethyl.

2. A compound according to claim 1 wherein one of the two

radicals is 1,2-benzenediyl.

3. A compound according to claim 1 wherein $R^1$ and $R^2$ are both methyl and n is 1 or 2.

4. A compound as claimed in claim 1 wherein the compounds is 2,3,3a,8-tetrahydro-N,N-dimethylisoxazolo[2,3-a]pyrrolo[2,1-c][1,4]benzodiazepine-2-methanamine;

2,3,3a,8-tetrahydro-N,N-dimethylimidazo[2,1-c]isoxazolo[2,3-a][1,4]benzodiazepine-2-methanamine;

2,3,3a,7-tetrahydro-N,N-dimethylisoxazolo[2,3-a]thieno[2,3-c][1]benzazepine-2-methanamine;

2,3,3a,7-tetrahydro-N,N-dimethylisoxazolo[2,3-a]thieno[3,2-c][1]benz-azepine-2-methanamine; a stereochemically isomeric form or a pharmaceutically acceptable addition salt thereof, or an N-oxide form thereof.

5. A composition comprising a pharmaceutically acceptable carrier and, as active ingredient, a therapeutically effective amount of a compound as claimed in claim 1.

6. A process of preparing a pharmaceutical composition comprising intimately mixing a pharmaceutically acceptable carrier with a therapeutically effective amount of the compound of claim 1.

7. A process of preparing a compound as described in claim 1, characterized in that:

a) a dienophile of formula (III) is reacted with an intermediate of formula (II):

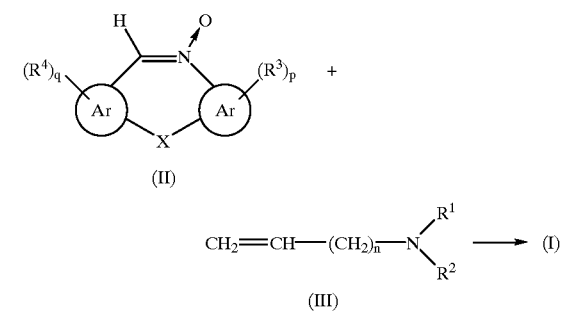

wherein in the intermediates (II) and (III) $R^1$ to $R^5$, X, n, r, p, q and

are defined as in claim 1, and the hydrogens on the sp$^2$-hybridized aliphatic carbon atoms may each individually be replaced by $R^5$;

b) converting compounds of formula (I) into each other following art-known transformations, and further, if desired, converting the compounds of formula (I), into a therapeutically active non-toxic acid addition salt by treatment with an acid, or into a therapeutically active non-toxic base addition salt by treatment with a base, or conversely, converting the acid addition salt form into the free base by treatment with alkali, or converting the base addition salt into the free acid by treatment with acid; and, if desired, preparing stereochemically isomeric forms or N-oxide forms thereof.

* * * * *